(12) United States Patent
Klug et al.

(10) Patent No.: US 12,181,403 B2
(45) Date of Patent: Dec. 31, 2024

(54) OPTICAL SENSOR CONTAINING A WAVEGUIDE WITH HOLOGRAPHIC ELEMENTS FOR MEASURING A PULSE AND BLOOD OXYGEN SATURATION

(71) Applicant: AUDI AG, Ingolstadt (DE)

(72) Inventors: Markus Klug, Ingolstadt (DE); Tobias Moll, Ingolstadt (DE); Johannes Scheuchenpflug, Baar-Ebenhausen (DE)

(73) Assignee: AUDI AG, Ingolstadt (DE)

( * ) Notice: Subject to any disclaimer, the term of this patent is extended or adjusted under 35 U.S.C. 154(b) by 421 days.

(21) Appl. No.: 17/608,257

(22) PCT Filed: Apr. 30, 2020

(86) PCT No.: PCT/EP2020/062091
§ 371 (c)(1),
(2) Date: Nov. 2, 2021

(87) PCT Pub. No.: WO2020/225111
PCT Pub. Date: Nov. 12, 2020

(65) Prior Publication Data
US 2022/0214269 A1    Jul. 7, 2022

(30) Foreign Application Priority Data
May 3, 2019    (DE) .................. 10 2019 206 361.6

(51) Int. Cl.
*G01N 21/25*    (2006.01)
*A61B 5/1455*   (2006.01)
*G01N 21/31*    (2006.01)

(52) U.S. Cl.
CPC ....... *G01N 21/255* (2013.01); *A61B 5/14552* (2013.01); *G01N 21/3151* (2013.01);
(Continued)

(58) Field of Classification Search
None
See application file for complete search history.

(56) References Cited

U.S. PATENT DOCUMENTS

| 5,088,817 A | 2/1992 | Igaki et al. |
| 10,146,053 B2 | 12/2018 | Yuan et al. |
| (Continued) | | |

FOREIGN PATENT DOCUMENTS

| CN | 1325285 A | 12/2001 |
| CN | 102822717 A | 12/2012 |
| (Continued) | | |

OTHER PUBLICATIONS

International Search Report dated Jul. 29, 2020, from International Application No. PCT/EP2020/062091, 4 pp.
(Continued)

*Primary Examiner* — Rufus L Phillips
(74) *Attorney, Agent, or Firm* — STAAS & HALSEY LLP

(57) ABSTRACT

A spectrometry device includes a carrier medium, or waveguide, for transmitting light by internal reflection, and a transceiver device that has at least one light source and a detection device. A transceiver deflection structure couples at least the light emitted by the light source into the carrier medium. A measurement deflection structure, arranged at a distance from the transceiver deflection structure, decouples the light out of the carrier medium onto a measuring surface of the carrier medium so that the biological tissue can reflect the light back to the carrier medium. The reflected light is transmitted back onto the detection device via the measurement deflection structure, the carrier medium and the transceiver deflection structure. The detection device determines an intensity signal of the reflected light which is used by an
(Continued)

analysis device to determine a pulse frequency signal and/or a pulse curve signal as a medical characteristic value.

18 Claims, 2 Drawing Sheets

(52) U.S. Cl.
CPC ............... *G01N 2021/3144* (2013.01); *G01N 2201/068* (2013.01); *G01N 2201/08* (2013.01)

(56) References Cited

U.S. PATENT DOCUMENTS

| | | | | |
|---|---|---|---|---|
| 2006/0119837 | A1* | 6/2006 | Raguin | G06V 40/1324 |
| | | | | 356/71 |
| 2008/0015424 | A1* | 1/2008 | Bernreuter | A61B 5/72 |
| | | | | 600/323 |
| 2009/0088611 | A1 | 4/2009 | Buschmann | |
| 2010/0022856 | A1* | 1/2010 | Cinbis | A61B 5/14542 |
| | | | | 600/310 |
| 2012/0229605 | A1 | 9/2012 | Pretorius et al. | |
| 2012/0310060 | A1 | 12/2012 | Baker, Jr. et al. | |
| 2013/0274611 | A1 | 10/2013 | Silveira et al. | |
| 2015/0310251 | A1* | 10/2015 | Wyrwas | G06V 40/1365 |
| | | | | 348/77 |
| 2016/0299077 | A1* | 10/2016 | Schleipen | G01N 21/6452 |
| 2017/0079591 | A1* | 3/2017 | Gruhlke | A61B 5/7278 |
| 2017/0191939 | A1* | 7/2017 | Carriere | G01N 21/65 |
| 2017/0220844 | A1* | 8/2017 | Jones | G06F 1/1637 |
| 2021/0228118 | A1* | 7/2021 | Friesen | A61B 5/6885 |
| 2021/0259597 | A1* | 8/2021 | Katnani | A61B 5/14553 |

FOREIGN PATENT DOCUMENTS

| | | |
|---|---|---|
| CN | 103619239 A | 3/2014 |
| CN | 105379306 A | 3/2016 |
| CN | 108024767 A | 5/2018 |
| DE | 10 2007 046 295 A1 | 4/2009 |
| DE | 10 2010 008 342 A1 | 8/2011 |
| DE | 10 2011 010 262 A1 | 8/2012 |
| EP | 2 932 729 B1 | 9/2016 |
| TW | 201032777 A1 | 9/2010 |
| WO | PCT/EP2020/062091 | 4/2020 |
| WO | WO 2020/225111 A1 | 11/2020 |

OTHER PUBLICATIONS

English translation by WIPO of International Preliminary Report on Patentability dated Sep. 7, 2021, from International Application No. PCT/EP2020/062091.

Jingjin Guo et al., "Design of a multiplexing grating for color holographic waveguide" Optical Engineering, Dec. 2015, 54(12), pp. 125105-1 to 125105-11.

Heerlein et al.; "Wearable-Medizintechnik: Lichtsensoren für die Selbstvermessung", Oct. 8, 2014, obtained from Wayback Machine pages captured in Nov. and Dec. 2020, 8 pp.

Chinese Office Action dated Jul. 19, 2023 for parallel Chinese Application No. 202080033523.X.

Office Action dated Jan. 30, 2020, from German Application No. 10 2019 206 361.6, 12 pp.

German Office Action dated Jan. 30, 2020, from German Application No. 10 2019 206 361.6.

\* cited by examiner

OPTICAL SENSOR CONTAINING A WAVEGUIDE WITH HOLOGRAPHIC ELEMENTS FOR MEASURING A PULSE AND BLOOD OXYGEN SATURATION

CROSS REFERENCE TO RELATED APPLICATIONS

This application is a U.S. national stage of International Application No. PCT/EP2020/062091, filed on Apr. 20, 2020. The International Application claims the priority benefit of German Application No. 10 2019 206 361.6 filed on May 3, 2019. Both the International Application and the German Application are incorporated by reference herein in their entirety.

BACKGROUND

Described below is a spectrometry device for noninvasive measurement of at least one medical characteristic value on biological tissue.

To determine a medical characteristic value of biological tissue, for example tissue of a human or animal body, it is often necessary to take a tissue sample and analyze it. The biological tissue can include epithelial tissue, connective and supporting tissue, muscle tissue, and nerve tissue. In addition, the biological tissue can also include tissue fluid, in particular blood, or the medical characteristic value can be, for example, a pulse rate and/or an oxygen saturation of the blood.

The determination of the pulse rate and/or the oxygen saturation of the blood can also be determined noninvasively, thus without taking tissue. For this purpose, determining a pulse frequency and an oxygen saturation of the blood noninvasively by a spectrometry device, in particular using a pulse oximeter, is known. Light having a predetermined wavelength is emitted into the biological tissue for the pulse frequency determination, wherein the light which has passed through the tissue or which was reflected from the tissue can subsequently be measured by a detector. The pulse frequency can then be determined from a change of the signal thus measured. To determine the oxygen saturation of the blood, in addition light having another predetermined wavelength can be emitted into the tissue and measured, so that the oxygen saturation of the blood can be ascertained using known methods. The measurement relates in particular to the radiation intensity of the light.

In known spectrometry devices for noninvasive measurement of a medical characteristic value on biological tissue, for example, a pulse oximeter, it is provided depending on the type of measurement that the light source and the detector have to be installed close to the measurement location, whereby a restriction results in the design of these spectrometry devices.

For noninvasive measurement of at least one medical characteristic value on biological tissue by a spectrometry device, the disadvantage related to the type of measurement of the short distance can be overcome.

SUMMARY

A spectrometry device for noninvasive measurement on biological tissue is described herein to measure at least one medical characteristic value on the biological tissue. Noninvasive means here in particular that no mechanical engagement in the tissue takes place. The spectrometry device includes a carrier medium which is designed to transmit or conduct light by internal reflection as a light guide, wherein a transceiver region and a measuring region, which is arranged offset along a longitudinal extension direction of the carrier medium with respect to the transceiver region and is provided for the application of the biological tissue, are provided on the carrier medium. In other words, a carrier medium is provided which can conduct light, for example, in a transparent solid by total reflection and which has a transceiver region and a measuring region which are arranged spaced apart in relation to one another, wherein biological tissue can be applied to the measuring region. Light can therefore be transmitted back and forth between the transceiver region and the measuring region by the carrier medium, whereby spacing apart of a light source and a detection device from tissue to be measured can be achieved. The biological tissue can in particular be a finger of a person whose medical characteristic value is to be measured. The medical characteristic value can be a pulse frequency and/or a blood oxygen saturation. The carrier medium can include a light guide made of glass or plastic or a combination of multiple light-guiding materials. It can be based on a plate or a rod or multiple plates in sandwich construction or a multilayered arrangement made up of films or lacquers.

This spectrometry device furthermore includes a transceiver device having at least one first light source and a detection device, wherein the first light source is designed and arranged to emit light having a first wavelength onto the transceiver region. The transceiver region is formed having a predefined transceiver deflection structure, which is designed to couple at least the light of the first wavelength emitted by the first light source into the carrier medium in the direction of the measuring region. This means that a first light source of the transceiver device emits light having a first wavelength onto the transceiver region of the carrier medium and a predefined transceiver deflection structure couples this light into the carrier medium, so that the coupled-in light can be deflected to the spaced-apart measuring region and relayed there. The first light source can be formed here as a light-emitting diode or laser diode which can emit light of the predefined wavelength.

The measuring region is formed having a predefined measuring deflection structure which is designed to decouple at least light coupled into the carrier medium in the direction of the measuring region, in particular the light of the first wavelength, from the carrier medium, so that when biological tissue is applied to a measuring surface of the carrier medium in the measuring region, the biological tissue reflects the decoupled light outside the carrier medium, and wherein the predefined measuring deflection structure is furthermore designed to receive the light reflected from outside the carrier medium and deflect or couple or diffract it in such a way that it is coupled back into the carrier medium in the direction of the decoupling region. The predefined transceiver deflection structure of the transceiver region is furthermore designed to decouple the light which is coupled from the measuring region back into the carrier medium in the direction of the decoupling region out of the carrier medium onto the detection device of the transceiver device, wherein the detection device is designed to determine a first intensity signal of the first wavelength. Furthermore, the spectrometry device includes an evaluation unit, which is designed to determine a pulse frequency signal and/or pulse curve signal as a medical characteristic value from a time curve of the first intensity signal.

In other words, light having a predefined wavelength is emitted by a first light source of the transceiver device onto the transceiver region of the carrier medium, wherein the transceiver region has a predefined transceiver deflection structure which couples the light into the carrier medium, where it is relayed by internal reflection through the carrier medium to the spaced-apart measuring region, at which the measuring deflection structure decouples the light coupled into the carrier medium from the carrier medium and can emit it onto an applied biological tissue, in particular a finger of a person. The light can then be reflected at the applied biological tissue and can be coupled via the predefined measuring deflection structure of the measuring region back into the carrier medium. The light coupled back into the carrier medium can then be conducted by internal reflection inside the carrier medium back to the predefined transceiver deflection structure of the transceiver region, where it is then decoupled onto the detection device of the transceiver device, which can determine an intensity signal of the first wavelength. An evaluation unit can subsequently determine a pulse frequency signal and/or a pulse curve signal as a medical characteristic value by a predefined determination method. A suitable determination method can be taken by a person skilled in the art from the known art, as was described at the outset.

The predefined transceiver deflection structure and the predefined measuring deflection structure can be formed as a diffraction structure or refraction structure, as an interference structure, grating structure, as a lens system or mirror. In particular, the transceiver deflection structure and the measuring deflection structure can each be formed as a holographic optical element (HOE) (or holographic element in short), which can deflect light having a predefined wavelength at a predefined angle. The detection device can be designed as a photodiode, for example as a CCD sensor or CMOS sensor, which can determine a light intensity or an intensity curve of the light. The evaluation unit, which can be designed as a computer processor, can subsequently recognize a periodic pattern in the intensity signal which can then be converted into a pulse frequency signal and can additionally or alternatively be displayed or output as a pulse curve signal.

The advantage results from the measuring region being spaced apart from the transceiver region, whereby a flatter structure of the measuring region can be achieved. In this way it is possible, for example, to arrange the measuring region as the measuring location of the biological tissue in a flat structure and thus enable a user easier access to the measuring region. Cleaning of the application surface of the finger in the measuring region is also simpler due to the spaced-apart arrangement, whereby the hygiene can be improved.

The described embodiments have additional advantages.

The first wavelength may be in a range from 600 nm to 800 nm, such as 660 nm. It is known here to a person skilled in the art that a wavelength specification does not exclusively specify a discrete wavelength, but rather that the wavelength specifies an optimal wavelength or peak wavelength, which can vary by a few nanometers. For example, in the case of the wavelength of 660 nm, a wavelength of +/−5% of the wavelength can also be meant. The first wavelength range specified here has the advantage that a light absorption of the biological tissue, in particular of human blood, has a desirable absorption or reflection characteristic.

One embodiment provides that the transceiver device furthermore includes a second light source, which is designed and arranged to emit light having a second wavelength onto the transceiver region, wherein the predefined transceiver deflection structure of the transceiver region is furthermore designed to couple the light of the second wavelength emitted by the second light source into the carrier medium in the direction of the measuring region. The detection device is furthermore designed to determine a second intensity signal of the second wavelength, wherein the evaluation unit is furthermore designed to determine a blood oxygen saturation as a medical characteristic value from the first intensity signal and the second intensity signal.

In other words, a second light source is provided in the transceiver device, which emits light having a second wavelength onto the transceiver region, the transceiver deflection structure of which can then couple the light having the second wavelength into the carrier medium. The first and the second wavelength differ. The light having the second wavelength is then transmitted to the measuring region in the carrier medium, wherein the transmitted light can be deflected at the measuring deflection structure onto biological tissue located in the measuring region. The light can then be reflected at the biological tissue and coupled back via the measuring deflection structure into the carrier medium, where it can then cover the path back to the transceiver deflection structure.

The transceiver deflection structure can then decouple the light of the second wavelength to the detection device, which can then determine a second intensity signal of the light of the second wavelength. The evaluation unit can determine a blood oxygen saturation as a medical characteristic value by a known method from the intensity signal of the first wavelength and the intensity signal of the second wavelength. Such a method was already described as available in the known art at the outset. The second light source can be designed as a light-emitting diode or laser diode and the transceiver deflection structure and the measuring deflection structure can be designed in such a way that they can couple and decouple light having the first and second wavelength into and out of the carrier medium. For this purpose, for example, a mirror arrangement, a lens arrangement, a diffraction structure, or a refraction structure, in particular a holographic optical element (HOE) can be provided. The advantage results due to this embodiment that in addition to a pulse frequency signal, a blood oxygen saturation can be determined.

The second wavelength may be in a range from 850 nm to 1000 nm, such as 940 nm. This is advantageous since an absorption or reflection characteristic of oxygen-poor to oxygen-rich blood has a different characteristic in this wavelength range than at the first wavelength. A concentration of oxygen-rich blood can thus be determined more accurately.

One embodiment provides that the detection device is designed to distinguish between the first wavelength and the second wavelength. This can be achieved, for example, in that the first light source and the second light source emit an alternating signal and the detection device can assign the intensity signal depending on the emitting light source. However, it can also be provided that the detection device has a beam splitter, which splits light incident on the detection device and can conduct it depending on the wavelength to different photodiodes. Alternatively or additionally, color filters can be used, which are arranged, for example, above at least two photosensors. The advantage results due to this embodiment that an improved intensity differentiation of the different wavelengths can be achieved, whereby a more accurate determination of the medical characteristic value can be achieved.

A further embodiment provides that the transceiver region and the transceiver device are housed in a housing protected from external light. In other words, the transceiver region and the transceiver device are housed in a light-opaque housing and only the carrier medium leads out of the housing to the measuring region, which is outside the housing. This means that only light which is coupled into the carrier medium is conducted to the transceiver device. The advantage results due to this embodiment that an influence of the ambient light on the transceiver device, in particular the detection device, can be minimized and thus an attenuation of background noise in the detection device can be achieved, whereby the determination of the medical characteristic value is improved.

One embodiment provides that the predefined transceiver deflection structure and the predefined measuring deflection structure have at least one optical grating.

Optical gratings, also called diffraction gratings, and the mode of operation and production method thereof are generally known. In principle, optical gratings can be formed as structures which are periodic at least in sections, so-called grating structures, in a substrate which can induce light guiding, for example, as is known from mirrors, lenses, or prisms, by the physical effect of diffraction. If light is incident, i.e., light beams are incident on the optical grating, wherein the incident light beams in particular fulfill the Bragg equation, the light beams are diffracted or deflected by the optical grating. The light guiding can therefore take place in particular due to interference events of the light beams diffracted by the optical grating. The deflection structure can accordingly also be referred to as a diffraction structure. A surface holographic grating and a volume holographic grating are holographic optical elements which can be produced in particular by a holography method.

An optical grating can be designed to be angle-selective or direction-selective and/or wavelength-selective or frequency-selective with respect to the incident light. Only light which is incident on an optical grating from a predetermined direction of incidence, for example, at a predetermined angle, can thus be deflected. Light which is incident from another direction on the optical grating may not deflected or deflected less the greater the difference is to the predetermined direction of incidence. Additionally or alternatively, only light of one wavelength or light which deviates at most by a predetermined wavelength range from the predetermined wavelength can be deflected by the optical grating at a defined angle of diffraction. In other words, for example, an optimal wavelength can be predefined at which only a component of the light in a defined wavelength or frequency range around the optimal wavelength is deflected by the optical grating (for example, a central optimal wavelength and a range having wavelength values up to +/−10% of the optimal wavelength); the remaining component of the light, in contrast, can propagate through the grating without being deflected. Therefore, at least one monochromatic light fraction can be split off from polychromatic light which is incident on the optical grating. The deflection effect therefore results in a frequency-selective and/or angle-selective manner, wherein the deflection effect is maximal for an optimal wavelength and decreases or becomes weaker toward longer and shorter wavelengths, for example, decreases according to a Gaussian bell. In particular, the deflection effect only acts on a fraction of the visible light spectrum and/or in an angle range less than 90°.

A further embodiment provides that the at least one optical grating is a surface holographic grating or a volume holographic grating which has a multiplex diffraction structure for at least the first and the second wavelength. Optical gratings can be produced by exposure of a substrate, thus, for example, by photolithography or holography. In this context, the optical gratings can then also be referred to as holographic or holographic optical gratings. Two types of holographic optical gratings are known: surface holographic gratings (SHG) and volume holographic gratings (VHG). In the case of surface holographic gratings, the grating structure can be created by optical deformation of a surface structure of the substrate. Incident light can be deflected, for example, reflected by the changed surface structure. Examples of surface holographic gratings are so-called sawtooth or blazed gratings. In contrast thereto, the grating structure in volume holographic gratings can be incorporated into the entire volume or a subsection of the volume of the substrate. Surface holographic gratings and volume holographic gratings are generally frequency-selective. However, optical gratings are also known which can diffract polychromatic light. These are referred to as multiplexed volume holographic gratings (MVHG) and can be produced, for example, by changing the periodicity of the grating structure of an optical grating or by arranging multiple volume holographic gratings in succession, whereby a multiplex diffraction structure results.

For example, glass in particular, quartz glass, is suitable as a material for a substrate for incorporating an optical grating. Alternatively or additionally, a polymer, in particular a photopolymer, or a film, in particular a photosensitive film, for example made of plastic or an organic material, can also be used. To use such substrates, it is additionally to be ensured that the material, in particular in substrate form, has flexible and light wave-conducting properties. Substrates which have a deflection structure for diffracting light, for example, in the form of an optical grating, can also be referred to as holographic optical elements (HOE).

A further embodiment provides that the measuring region and the transceiver region are incorporated directly into the carrier medium, in particular into a surface structure of the carrier medium. An alternative embodiment provides that the carrier medium is formed as a separate element from the measuring region and the transceiver region. In the first case, the measuring region and the transceiver region can thus be incorporated, for example, directly into a surface structure of the carrier medium. The carrier medium itself can thus be formed as a HOE, for example, etched or lasered. In the second case, the measuring region, the transceiver region, and the carrier medium can be formed separately. The measuring region and the transceiver region can form at least one first element, for example, and the carrier medium can form a second element which presses against the first element. The measuring region and the transceiver region can thus be formed in at least one HOE. This enables a greater selection in the use of a carrier medium. For example, the measuring region and the transceiver region can be formed in different sections of a holographic film or plate. The film or plate can be adhesively bonded on the carrier medium to fasten the film or plate on the carrier medium. Alternatively, the holographic film can also be formed as an adhesion film and can adhere directly, thus without adhesive, due to molecular forces on the surface of the carrier medium.

The features of the described embodiments may be combined if they were not explicitly indicated as opposing alternatives.

BRIEF DESCRIPTION OF THE DRAWINGS

These and other aspects and advantages will become more apparent and more readily appreciated from the following description of the exemplary embodiments, taken in conjunction with the accompanying drawings of which.

DETAILED DESCRIPTION

In the exemplary embodiments explained hereinafter, the described components of the embodiments each represent individual features to be considered independently of one another, which each also refine the invention independently of one another. The disclosure is therefore also to include combinations of the features of the embodiments other than those shown. Furthermore, the described embodiments can also be supplemented by further features already described.

In the figures, identical reference signs each identify functionally identical elements.

Figure 1:
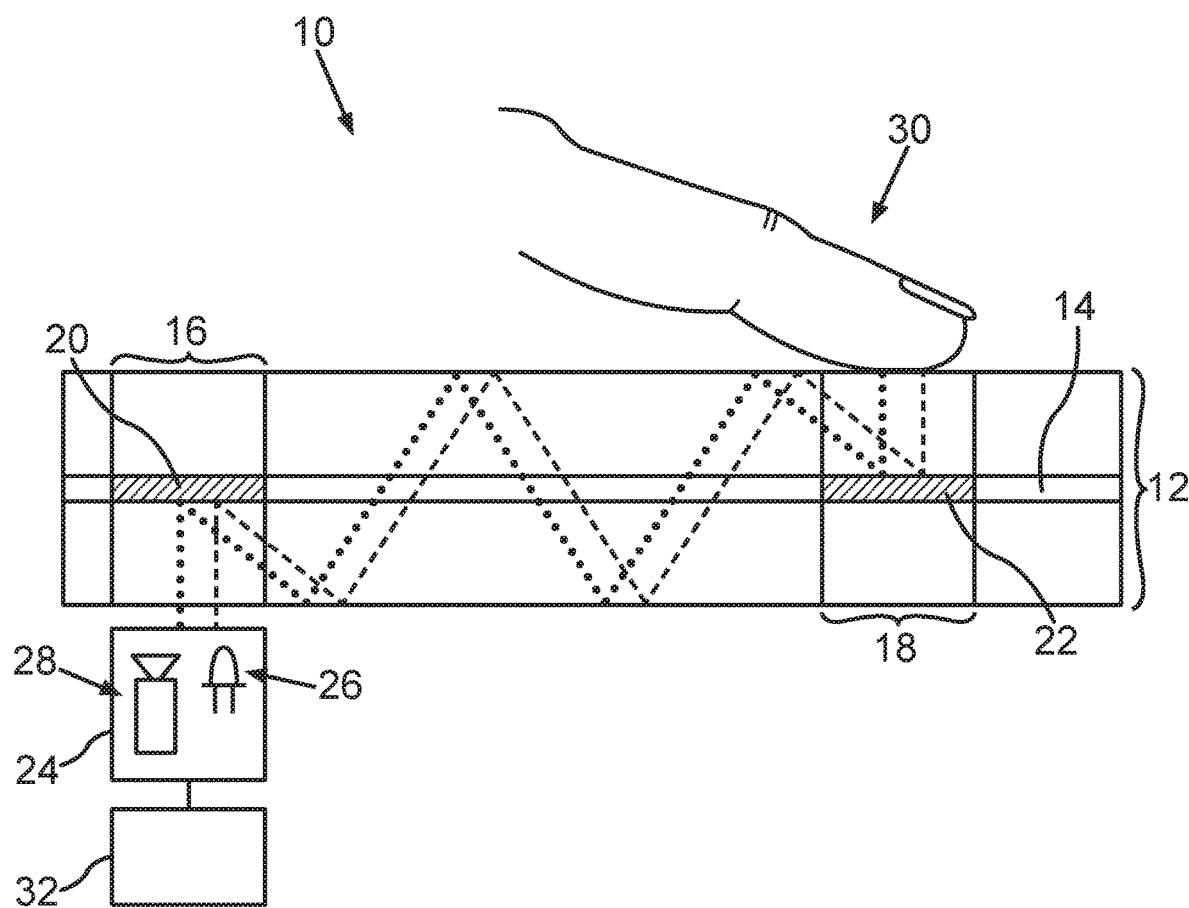
FIG. 1 is a schematic side view of a spectrometry device according to a first exemplary embodiment.

FIG. 1 shows a schematic illustration of a spectrometry device 10 for noninvasive measurement of at least one medical characteristic value on biological tissue. The spectrometry device 10 includes a carrier medium 12, which is formed as a light guide for transmitting coupled-in light by internal reflection.

The carrier medium 12 is formed in this case using separate cuboid elements, thus plates, which are constructed in a sandwich design to form the carrier medium. The carrier medium 12 includes, for example, two plastic plates or glass plates here, which are used as the light guide and form the cover layers of the carrier medium. A core of the carrier medium can be formed, for example, by a holographic optical element, which is referred to here as the holographic element 14, and which can be formed, for example, as a transparent photopolymer film. The glass plates press directly with a respective surface on each of opposing surfaces of the holographic element. In other words, the holographic element 14 and the glass plates press flatly against one another with their respective faces enclosed by a length side and a width side. FIG. 1 shows in particular a sectional view of the spectrometry device 10, in which the spectrometry device 10 is shown with a section along a longitudinal axis.

The carrier medium 12 can include a transceiver region 16 and a measuring region 18, which are arranged offset along a longitudinal extension direction of the carrier medium. In particular, the transceiver region 16 and the measuring region 18, as shown in this embodiment, can be formed at different ends in a longitudinal direction of the carrier medium.

The holographic element 14, which is located in the transceiver region 16, can have been exposed by a holography method, whereby a predefined transceiver deflection structure 20 can form, which can be formed in particular as a volume holographic grating. This means that the transceiver deflection structure 20 has a grating structure which can diffract light having a predefined wavelength at a predetermined angle.

Similarly thereto, the holographic element 14 can have been exposed in the measuring region 18 using a holography method, whereby a measuring deflection structure 22 can form, which is also formed in this example as a volume holographic grating.

A transceiver device 24, which is arranged, for example, centrally on one of the glass plates of the carrier medium in the transceiver region, can be provided on a surface of the carrier medium in the transceiver region 16. The transceiver device 24 can include a first light source 26, which is designed to emit light having a first wavelength onto the transceiver region 16. In particular, the first light source 26 can have a light-emitting diode or a laser diode, which emits light having a first wavelength, wherein the light having the first wavelength can be in a range from 600 nm to 800 nm, in particular at 660 nm. Furthermore, a detection device 28 can be provided in the transceiver device 24, which is light-sensitive and can determine at least one first intensity signal of the first wavelength. For example, the detection device 28 can have a photodiode which can change a photocurrent upon exposure in dependence on the intensity of the incident light, whereby a first intensity signal is determinable.

A mode of operation of the spectrometry device 10 shown in FIG. 1 is to be explained on the basis of an example hereinafter. In the exemplary embodiment shown in FIG. 1, it can be provided that a pulse frequency is to be determined as a medical characteristic value. For this purpose, the first light source 26 of the transceiver device 24 can emit, for example, light having a wavelength of 660 nm into the transceiver region 16 of the carrier medium 12, which is indicated as a dashed line in the figure. The light of the first wavelength can then be diffracted at the volume holographic grating of the transceiver deflection structure 20 in such a way that the light is coupled into the carrier medium 12 in the direction of the measuring region and is transmitted by internal reflection, that is to say total reflection, to the measuring region 18 (dashed line).

In the measuring region 18, the volume holographic grating of the measuring deflection structure 22 can then diffract the light in the direction of a surface of the carrier medium, wherein a finger 30 rests on the surface of the carrier medium, for example, as biological tissue to be measured. The light emitted onto the finger, in particular the light having the wavelength of 660 nm, can enter the biological tissue and can be scattered and thus reflected, for example, at blood inside the finger 30. The reflected light, which is indicated as a dotted line, can then enter back into the measuring region 18 and can be coupled by the measuring deflection structure 22 back into the carrier medium 12, where it is then conducted back to the transceiver region 16 and can be decoupled by the transceiver deflection structure 20 onto the transceiver device 24. The detection device 28 can then record the light of the first wavelength of 660 nm reflected from the finger 30 as an intensity signal, wherein the intensity signal can change periodically in accordance with a pulse of the blood flowing through the finger 30.

An evaluation unit 32 can then determine a pulse frequency signal from the intensity signal, for example, by a Fourier analysis of the intensity signal.

Figure 2:
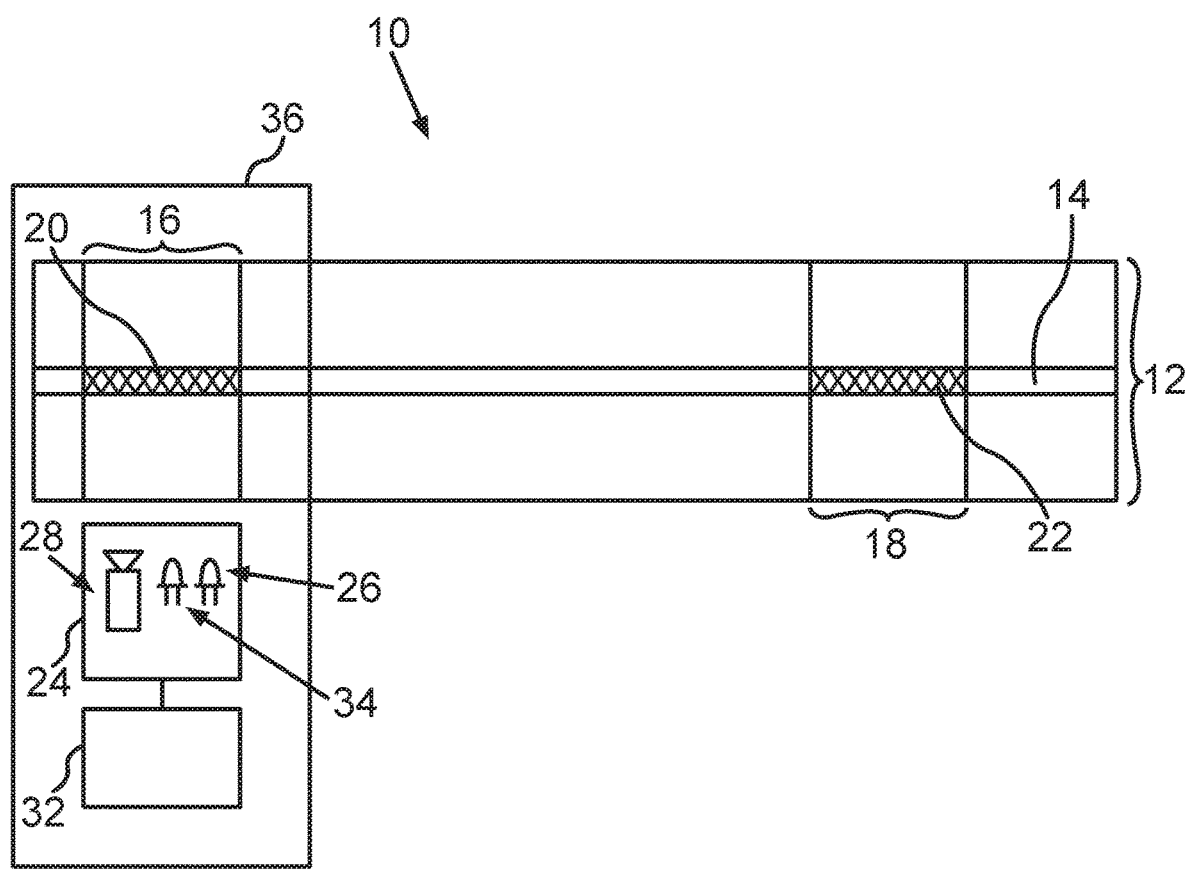
FIG. 2 is a schematic side view side view a spectrometry device according to a second exemplary embodiment.

A spectrometry device 10 according to a second exemplary embodiment is shown in FIG. 2. In the general structure, the second spectrometry device 10 is designed identically to the spectrometry device according to the first embodiment, i.e., having the carrier medium 12 which is formed in a sandwich construction having two glass panes as cover layers and the holographic optical element 14 in between. Furthermore, the spectrometry device 10 of the second embodiment has the transceiver device 24 and the transceiver region 16 and the measuring region 18.

In addition to the first embodiment of the spectrometry device 10, the transceiver device 24 includes, in addition to the first light source 26, a second light source 34, which can be designed as a light-emitting diode or laser diode and can emit a second wavelength in a range from 850 nm to 1000 nm, such as 940 nm.

In the second embodiment, the predefined transceiver deflection structure 20 and the predefined measuring deflection structure 22 can have a volume holographic grating, which is formed in this embodiment as a multiplex diffraction structure. The multiplex diffraction structure means that the holographic optical element 14 has been exposed during the production in the transceiver region or measuring region in such a way that two grating structures can be created interlaced with one another, so that a Bragg angle can result for the respective wavelength used, which only diffracts the wavelengths of the first and second light source 26, 34 at the predetermined angle, so that only this light can be coupled into and decoupled from the carrier medium 12. The multiplex diffraction structure can also have successive volume gratings, wherein for this purpose respective successive volume gratings are formed for a predefined wavelength. In this way, the advantage results that only light having the respective predefined wavelength is coupled into the carrier medium 12 and ambient light which does not contribute to the measurement can be filtered out, whereby signal noise at the detection device 28 can be reduced.

The detection device 28 can be designed in this embodiment to distinguish between the first wavelength and the second wavelength. This can be achieved, for example, by beam splitters or color filters in the detector. By discrimination of the wavelengths inside the detection device 28, a first intensity signal of the first wavelength and a second intensity signal of the second wavelength can then be determined, from which reflection or absorption characteristics of the biological tissue, in particular the blood, can be determined in different spectral ranges. A blood oxygen saturation can then be determined therefrom by the evaluation unit 32 by known methods as a medical characteristic value.

To protect the detection device 28 from outside light, which can interfere with the measurement, in addition a housing 36 can be provided, which is produced from a light-opaque, i.e., light-absorbing material. For example, the housing 36 can be a matte plastic housing or a housing made of metal. The housing 36 is not restricted to the second embodiment, but rather can also be provided for the first embodiment.

Using the spectrometry device 10 according to one of the two embodiments, the measuring region 18 can be arranged remotely from the transceiver region 16, whereby a flatter structure can result, which saves space and enables a better access to the measuring region.

Overall, the examples show how a pulse oximetry can be achieved via a holographic optical element.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide* v. *DIRECTV*, 358 F3d 870, 69 USPQ2d 1865 (Fed. Cir. 2004).

The invention claimed is:

1. A spectrometry device for noninvasive measurement of at least one medical characteristic value on biological tissue, comprising:

a carrier medium, formed as a light guide for transmitting coupled-in light by internal reflection, having a transceiver region and a measuring region arranged offset along a longitudinal extension direction of the carrier medium with respect to the transceiver region and provided for application of the biological tissue;

a transceiver device having a detector and at least one first light source to emit first light having a first wavelength onto the transceiver region of the carrier medium, the transceiver device further comprising a second light source to emit second light having a second wavelength different than the first wavelength onto the transceiver region of the carrier medium, the transceiver region having a predefined transceiver deflector to couple at least the first light emitted by the first light source into the carrier medium towards the measuring region, and to couple the second light emitted by the second light source into the carrier medium towards the measuring region, the measuring region having a predefined measuring deflector configured to decouple the first light out of the carrier medium towards a measuring surface of the carrier medium in the measuring region, the biological tissue reflecting the first light back to the carrier medium when the biological tissue is applied to the measuring surface, and couple the first light reflected from the biological tissue back into the carrier medium towards the predefined transceiver deflector of the transceiver region where the first light is decoupled out of the carrier medium onto the detector of the transceiver device, and the detector configured to determine a first intensity signal of the first wavelength and to determine a second intensity signal of the second wavelength; and an evaluator configured to determine at least one of a pulse frequency signal and a pulse curve signal as a medical characteristic value based on a time curve of the first intensity signal and to determine a blood oxygen saturation as a medical characteristic value from the first intensity signal and the second intensity signal, wherein each of the predefined transceiver deflector and the predefined measuring deflector have at least one optical grating, and the at least one optical grating is one of a surface holographic grating and a volume holographic grating having a multiplex diffraction structure for at least the first wavelength and the second wavelength.

2. The spectrometry device as claimed in claim 1, wherein the first wavelength is in a range from 600 nm to 800 nm.

3. The spectrometry device as claimed in claim 2, wherein the first wavelength is 660 nm.

4. The spectrometry device as claimed in claim 2, wherein the second wavelength is in a range of 850 nm to 1000 nm.

5. The spectrometry device as claimed in claim 4, wherein the second wavelength is 940 nm.

6. The spectrometry device as claimed in claim 4, wherein the detector is configured to distinguish between the first wavelength and the second wavelength.

7. The spectrometry device as claimed in claim 6, further comprising a housing configured to protect the transceiver region and the transceiver device from outside light.

8. The spectrometry device as claimed in claim 7, wherein the housing is light-opaque, and each of the predefined transceiver deflector and the predefined measuring deflector have at least one frequency-selective optical grating.

9. The spectrometry device as claimed in claim 7, wherein the at least one optical grating is configured to diffract only a partial range of visible light within a predefined wavelength range at a predetermined angle in dependence on a grating constant.

10. The spectrometry device as claimed in claim 9, wherein the measuring region and the transceiver region are one of incorporated directly into a surface structure of the carrier medium, and formed separately from the carrier medium.

11. The spectrometry device as claimed in claim 1, wherein the second wavelength is in a range of 850 nm to 1000 nm.

12. The spectrometry device as claimed in claim 1, wherein the detector is configured to distinguish between the first wavelength and the second wavelength.

13. The spectrometry device as claimed in claim 1, further comprising a housing configured to protect the transceiver region and the transceiver device from outside light.

14. The spectrometry device as claimed in claim 1, wherein each of the predefined transceiver deflector and the predefined measuring deflector have at least one frequency-selective optical grating.

15. The spectrometry device as claimed in claim 14, wherein the at least one optical grating is configured to diffract only a partial range of visible light within a predefined wavelength range at a predetermined angle in dependence on a grating constant.

16. The spectrometry device as claimed in claim 1, wherein
  each of the predefined transceiver deflector and the predefined measuring deflector have at least one optical grating, the at least one optical grating is one of a surface holographic grating and a volume holographic grating having a multiplex diffraction structure for at least the first wavelength and the second wavelength, and the at least one optical grating is frequency-selective.

17. The spectrometry device as claimed in claim 1, wherein the measuring region and the transceiver region are one of incorporated directly into a surface structure of the carrier medium, and formed separately from the carrier medium.

18. A spectrometry device for noninvasive measurement of at least one medical characteristic value on biological tissue, comprising:
  a carrier medium, formed as a light guide for transmitting coupled-in light by internal reflection, having a transceiver region and a measuring region arranged offset along a longitudinal extension direction of the carrier medium with respect to the transceiver region and provided for application of the biological tissue;
  a transceiver device having a detector and at least one first light source to emit first light having a first wavelength onto the transceiver region of the carrier medium,
  the transceiver region having a predefined transceiver deflector to couple at least the first light emitted by the first light source into the carrier medium towards the measuring region,
  the measuring region having a predefined measuring deflector configured to
    decouple the first light out of the carrier medium towards a measuring surface of the carrier medium in the measuring region, the biological tissue reflecting the first light back to the carrier medium when the biological tissue is applied to the measuring surface, and
    couple the first light reflected from the biological tissue back into the carrier medium towards the predefined transceiver deflector of the transceiver region where the first light is decoupled out of the carrier medium onto the detector of the transceiver device, and
  the detector configured to determine a first intensity signal of the first wavelength; and
  an evaluator configured to determine at least one of a pulse frequency signal and a pulse curve signal as a medical characteristic value based on a time curve of the first intensity signal,
wherein
  the at least one optical grating is one of a surface holographic grating and a volume holographic grating having a multiplex diffraction structure for at least the first wavelength,
  the first wavelength is in a range from 600 nm to 800 nm,
  the transceiver device further comprises a second light source to emit second light having a second wavelength onto the transceiver region of the carrier medium,
  the predefined transceiver deflector of the transceiver region is configured to couple the second light emitted by the second light source into the carrier medium towards the measuring region,
  the detector is configured to determine a second intensity signal of the second wavelength,
  the evaluator is configured to determine a blood oxygen saturation as a medical characteristic value from the first intensity signal and the second intensity signal,
  the second wavelength is in a range of 850 nm to 1000 nm,
  the detector is configured to distinguish between the first wavelength and the second wavelength,
the spectrometry device further comprising a housing configured to protect the transceiver region and the transceiver device from outside light,
wherein
  each of the predefined transceiver deflector and the predefined measuring deflector have at least one optical grating, and
  the at least one optical grating is one of a surface holographic grating and a volume holographic grating having a multiplex diffraction structure for at least the first wavelength and the second wavelength.

* * * * *

UNITED STATES PATENT AND TRADEMARK OFFICE
CERTIFICATE OF CORRECTION

| | |
|---|---|
| PATENT NO. | : 12,181,403 B2 |
| APPLICATION NO. | : 17/608257 |
| DATED | : December 31, 2024 |
| INVENTOR(S) | : Markus Klug et al. |

It is certified that error appears in the above-identified patent and that said Letters Patent is hereby corrected as shown below:

In the Specification

Column 1, Line 10, Delete "20," and insert -- 30, --.

Signed and Sealed this
Twenty-fifth Day of March, 2025

Coke Morgan Stewart
*Acting Director of the United States Patent and Trademark Office*